United States Patent [19]
Danno et al.

[11] Patent Number: 5,716,797
[45] Date of Patent: Feb. 10, 1998

[54] STABLE TWO-PART REAGENT FOR THE MEASUREMENT OF CREATINE KINASE ACTIVITY

[75] Inventors: Masakazu Danno; Toshiro Hanada, both of Amagasaki, Japan

[73] Assignee: Wako Pure Chemical Industries, Ltd., Osaka, Japan

[21] Appl. No.: 585,516

[22] Filed: Jan. 16, 1996

[30] Foreign Application Priority Data

Jan. 13, 1995 [JP] Japan .................................. 7-021094

[51] Int. Cl.$^6$ .................................................. C12Q 1/50
[52] U.S. Cl. ................................................ 435/17; 435/194
[58] Field of Search ........................................ 435/17, 194

[56] References Cited

U.S. PATENT DOCUMENTS 4,740,458  4/1988  Kondo et al. ............................ 435/15

FOREIGN PATENT DOCUMENTS 5-38600  6/1993  Japan .

OTHER PUBLICATIONS

L.G. Morin, "Creatine Kinase: Re–examination of Optimum Reaction Conditions", Clinical Chemistry, vol. 23, No. 9, 1997, pp. 1569–1575.
Recommendations of the German Society for Clinical Chemistry, J. Clin. Chem. Clin. Biochem., vol. 15, 1977, No. 4, pp. 255–260.
W. Gerhardt et al., "EDTA effect on creatine kinase (CK) and on the SCE reagent", Scand. J. Clin. Lab. Invest., vol. 39, 1979, pp. 737–742.
International Federation of Clinical Chemistry Scientific Division, Ann. Biol. Clin., 1990, 48, pp. 185–202.
Database WPI, Sec. Ch, Week 8709, Derwent Publications Ltd., London, GB; Class B04, AN 87–059050, JP–A–61 187 657 (Wako Pure Chem IND KK), Aug. 21, 1986, Abstract.
Database WPI, Sec. Ch, Wk 8451, Derwent Pub. Ltd., London, GB, Class B04, AN84–316068, JP–A–59 198 999 (Denka Seiken KK) Nov. 10, 1984.
Database WPI, Sec. Ch., Week 9323, Derwent Pub. Ltd., London G.B., Class B04, AN 93–184816, JP–A–05 111 396, Oriental Yeast Co. Ltd. May 7, 1993, Abstract.
Annales De Biologie Clinique, vol. 48, No. 3, 1990, Paris, pp. 185–191, Horder, ". . . IFCC Method for Creatine Kinase", XP002007526.

*Primary Examiner*—Sandra E. Saucier
*Attorney, Agent, or Firm*—Armstrong, Westerman, Hattori, McLeland & Naughton

[57] ABSTRACT

A stable two-part liquid reagent composition for measuring creatine kinase activity contains, in the first part, adenosine 5'-adiphosphate, kexokinase or glucokinse, nicotinamide adenine dinucleotide (phosphate), glucose-6-phosphate dehydrogenase, and thioglycerol, 2-mercaptoethanol, or 2-mercaptoethanesulfonic acid or a salt thereof; and contains, the second part, creatine phosphate at a pH of 7.5 to 10.0. Glucose and magnesium ions can be included in either part or in both parts. The two-part composition is stable even after being stored for 3 months at 10° C.

7 Claims, No Drawings

STABLE TWO-PART REAGENT FOR THE MEASUREMENT OF CREATINE KINASE ACTIVITY

BACKGROUND OF THE INVENTION

This invention relates to a liquid reagent for measuring creatine kinase (hereinafter abbreviated as CK) activity in a body fluid such as serum.

In a living body, CK is present in skeletal muscle in the largest amount and in brain and cardiac muscle in the second largest amount. CK is present also in smooth muscle and nervous systems, but its content in liver, kidney, erythrocyte, etc. is very low. Since an increase of CK activity was found in 1959 in the serum of a patient with muscular dystrophy, CK activity measurement has been clinically applied. At present, in the field of clinical examinations, the CK activity measurement is an important item usually carried out for diagnoses of muscular diseases, heart deseases, etc.

On the other hand, CK is rapidly inactivated in serum, and hence CK activity is usually measured after reactivating CK with a reactivator added to a reagent for measuring the activity.

As the CK reactivator, there are usually used so-called SH group-containing compounds (hereinafter abbreviated as SH compound) such as N-acetylcysteine (hereinafter abbreviated as NAC), dithiothreitol (hereinafter abbreviated as DTT), glutathione, etc. Various SH compounds have been investigated as the CK reactivator.

For example, as the CK reactivator, Hess used cysteine in 1968, Warren used DTT in 1972 and Szats used NAC in 1976 [Clin. Chem., vol. 23, 1569–1575 (1977)].

Further, Morin reported in 1977 that thioglycerol (hereinafter abbreviated as TG) and mercaptoethanol are suitable as the CK reactivator [Clin. Chem., Vol. 23, 1569–1575 (1977)]. However, in this reference, only a preincubation time required for reactivating CK activity and the CK-reactivating ability in stored serum were investigated, and the storage stability at liquid state of a reagent for CK activity measurement containing such an SH compound as the CK reactivator was not investigated at all. However, those skilled in the art have considered that the reagent for CK activity measurement should be used in a short time because it is poor in storage stability at liquid state and has a very short lifetime at room temperature (18°–37° C.) after dissolving in a solution as described in JP-B 5-38600 (from column 3, line 39 to column 4, line 18).

In various countries, recommendable methods for measuring CK activity have been chosen by institutions such as various academic societies, and the kind of the CK reactivator, etc. have been chosen together with various measuring conditions. For example, reduced-form glutathione (hereinafter abbreviated as GSH) was chosen by German Society for Clinical Chemistry (GSCC) in 1970. Further, in 1977, NAC was selected as the CK reactivator from 27 SH compounds including the above conventional SH compounds, in view of reactivating ability, stability at dry state and in a working solution, interference by other serum enzymes, appearance of turbidity by coexistence with serum, odor, cost, etc. (J. Clin. Chem. Clin. Biochem., Vol. 15, 255–260 (1977)].

However, when NAC is used as the reactivator, the SH group of NAC in liquid state is gradually oxidized because of the relatively low stability of NAC, so that NAC cannot retain its effect as the CK reactivator for a long period of time. Moreover, oxidized product of NAC inhibits CK activity [Scand. J. Clin. Lab. Invest., Vol. 39, 737–742 (1979)] and hence is a serious cause of not only the deterioration of the reactivating ability but also the deterioration of the stability at liquid state of a reagent for measuring CK activity.

For coping with such problems in the employment of NAC as the CK reactivator, various studies were conducted. As a result, it was found that when ethylenediaminetetraacetic acid (hereinafter abbreviated as EDTA) was added to a reagent for measuring CK activity, the stability of NAC was increased and the production of the oxidized product having inhibitory effect on CK activity was prevented. From such a result, Scandinavian Society for Clinical Chemistry and Clinical Physiology (SSCC & CP), and Japanese Society for Clinical Chemistry (JSCC) employed simultaneous use of EDTA and NAC. Further, International Federation for Clinical Chemistry (IFCC) also employed the simultaneous use of EDTA and NAC. [Rinsho-Kagaku, Vol. 19, No. 2, pp. 184–208 (1990), Ann. Biol. Clin., 1990, 48, p185–202]. However, a reagent for CK activity measurement containing both EDTA and NAC is not always sufficient in stability at liquid state.

Accordingly, a method comprising adding both NAC and an SH compound other than NAC to a reagent for measuring CK activity has also been proposed (JP-B 5-38600) but can not improve the stability of the reagent sufficiently.

On the other hand, the recent trend of agents for clinical examinations is as follows: for removing the problems in conventional reagents for clinical examinations supplied in freeze-dried state (i.e. a decrease in work efficiency, an increase in cost, etc., which are caused by mistakes in preparation of a reagent due to much labor and troublesome operations required for preparing the reagent), and for making it possible to take a rapid measure in an urgent examination, liquid reagents which do not require the labor of preparing them and can be stored for a long period of time are becoming leading agents for clinical examinations at present in place of conventional reagents prepared by dissolving the freeze-dried reagent properly in a buffer solution or the like. Also in the case of a reagent for measuring CK activity, there is desired the development of a liquid reagent which can be stored for a long period of time.

SUMMARY OF THE INVENTION

The present invention was made in view of such conditions and is intended to provide a liquid reagent for measuring CK activity, which can be stored for a long period of time.

The present invention provides a liquid reagent for measuring CK activity which comprises at least one compound selected from the group consisting of thioglycerol (TG), 2-mercaptoethanol (hereinafter abbreviated as 2ME), and 2-mercaptoethanesulfonic acid (2MES) or its salt, said liquid reagent being stable for a long period of time.

The present invention also provides a liquid reagent composition for measuring CK activity which comprises a first reagent comprising ADP, HK or GK, NAD or NADP, G6PDH and at least one compound selected from the group consisting of TG, 2ME, and 2MES or its salt, and a second reagent comprising CP, and having a pH of 7.5 to 10, and glucose and magnesium ion being separately or in combination incorporated in either one or both of the first reagent and the second reagent.

Further, the present invention provides a liquid reagent kit for measuring CK activity which comprises a combination of a first reagent container containing imidazole-acetate buffer, magnesium acetate, sodium azide, NADP, HK, G6PDH, ADP, adenosine 5'-monophosphate (hereinafter abbreviated as AMP), TG, diadenosine penta- phosphate (hereinafter abbreviated as AP$_5$A), glucose and EDTA, and a second reagent container containing N,N-bis(2-hydroxyethyl)glycin (hereinafter abbreviated as Bicine)-sodium hydroxide buffer, magnesium acetate, sodium azide, EDTA, glucose and CP within a pH range of 7.5 to 10.

DESCRIPTION OF PREFERRED EMBODIMENTS

The stabilized liquid reagent for measuring creatine kinase activity of the present invention comprises at least one compound selected from the group consisting of thioglycerol (TG), 2-mercaptoethanol (2ME), and 2-mercaptoethanesulfonic acid (2MES) or its salt, and as a stabilizer therefor preferably EDTA and salts thereof mentioned below.

Even if added to a high concentration, any of the above-mentioned compounds used as a CK reactivator in the liquid reagent for measuring CK activity of the present invention does not inhibit CK activity. Therefore, the concentration of the above-mentioned compounds used in a reaction solution for measuring CK activity is not particularly limited so long as it is higher than the lowest concentration at which CK reactivating ability can be attained. For example, when TG is used as a CK reactivator, its concentration is as follows: TG is incorporated into the liquid reagent for measuring CK activity so that the TG concentration in a reaction solution for measuring CK activity may be usually 10 mM or more. For economical benefit, the concentration is properly chosen in the range of preferably 10 to 260 mM.

When 2ME is used as a CK reactivator, its concentration is as follows: 2ME is incorporated into the liquid reagent for measuring CK activity so that the 2ME concentration in a reaction solution for measuring CK activity may be usually 5 mM or more. For economical benefit, the concentration is properly chosen in the range of preferably 5 to 80 mM.

When 2MES or its salt is used as a CK reactivator, the concentration of 2MES or its salt is as follows: 2MES or its salt is incorporated into the liquid reagent for measuring CK activity so that the concentration of 2MES or its salt in a reaction solution for measuring CK activity may be usually 5 mM or more. For economical benefit, the concentration is properly chosen in the range of preferably 5 to 80 mM. Preferable examples of the salt of 2MES are alkali metal salts such as Na salt, K salt, Li salt, etc.

Needless to say, the above-mentioned compounds may be used singly or in proper combination when one or more CK reactivators are used in the liquid reagent for measuring CK activity of the present invention.

In the liquid reagent composition for measuring CK activity of the present invention, the same reagents as used in conventional methods for measuring CK activity by reactivating CK activity can be used except for using as CK reactivator at least one compound selected from the group consisting of TG, 2ME, and 2MES or its salt. As such methods for measuring CK activity, there can be exemplified methods of quantitating CP or ADP produced by the rightward reaction (the forward reaction) in the following reaction catalyzed by CK:

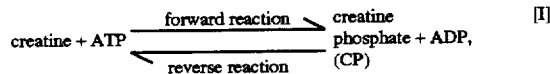

for example, (1) a method of measuring CP on the basis of the increase of inorganic phosphoric acid produced by hydrolysis of CP, (2) an ultraviolet region method (Tanzer-Gilvarg method) which comprises reacting ADP with phosphoenolpyruvic acid (hereinafter abbreviated as PEP) in the presence of pyruvate kinase (hereinafter abbreviated as PK), reacting the resulting pyruvic acid with NADH in the presence of lactate dehydrogenase, and measuring the increase of NADH, and (3) a method (Nuttal-Weldin method) which comprises reacting ADP with PEP in the presence of PK, reacting the resulting pyruvic acid with 2,4-dinitrophenylhydrazine, and determining the resulting hydrazone colorimetrically; and methods of quantitating creatine or ATP produced by the leftward reaction (the reverse reaction) in the above-mentioned reaction catalyzed by CK, for example, (4) a method (Hughes method) which comprises colorimetric determination of creatine by use of β-naphtholdiacetyl reaction, or a method (Conn-Anido method) which comprises reacting creatine with ninhydrin, followed by fluorometry of the condensation product of creatine and ninhydrin, (5) a method using luciferase (JP-A 51-41597, JP-A 55-120796, JP-A 56-26200 and JP-A 57-105199), (6) a method using phosphoglycerate kinase and glyceraldehyde-3-phosphate dehydrogenase (JP-B 59-34119 and JP-A 56-155000), and (7) a method of using HK and G6PDH, that is, an ultraviolet region method which comprises reacting ATP with glucose in the presence of HK to produce glucose-6-phosphoric acid, which is further reacted with NAD (or NADP) in the presence of G6PDH, and measuring the produced NADH (or NADPH) at 340 nm.

Of these conventional measuring methods, the measuring method (7) is especially preferable in the case of the liquid reagent for measuring CK activity of the present invention because it is on an excellent principle, is good in sensitivity and reproducibility, and makes it possible to deal with a large number of samples by means of an autoanalyzer.

A typical example of the liquid reagent composition for measuring CK activity of the present invention is one which is prepared using at least one compound selected from the group consisting of TG, 2ME, and 2MES or its salt as a CK reactivator, and other main components such as CP, ADP, glucose, HK or GK, NAD (or NADP), G6PDH, a magnesium ion, etc.

The liquid reagent composition for measuring CK activity preferably contains one or more chelating agents for stabilizing the SH compound and preventing the reagent from coloring in an effective concentration. Examples of such chelating agents are EDTA, trans-1,2-diaminocyclohexane-N,N,N',N'-tetraacetic acid monohydrate, 1,3-diamino-2-hydroxypropane-N,N,N',N'-tetraacetic acid, ethylenediamine-N,N'-diacetic acid, N-(2-hydroxyethyl)iminodiacetic acid, N-(2-hydroxyethyl)-iminodiacetic acid, and salts thereof, e.g. alkali metal salts thereof, ammonium salts thereof.

Needless to say, the liquid reagent composition for measuring CK activity of the present invention may, if necessary, contain the following reagents usually used in a method for measuring CK activity, in a concentration range usually employed in the art: for example, antiseptics such as sodium azide, etc.; surfactants preferably nonionic surfactants such as polyoxyethylene octylphenyl ether (Triton X-100), polyoxyethylene lauryl ether (Emulgen 120), etc.; buffers such as imidazole buffer, bis(2-hydroxyethyl)-iminotris (hydroxymethyl)methane (Bis-Tris) buffer, etc.; and adenylate kinase (hereinafter abbreviated as AK) inhibitors for avoiding the influence of AK activity which is present in a body fluid sample and causes positive errors in the measurement of CK activity, such as AMP, diadenosine polyphosphates [e.g. diadenosine tetraphosphate (hereinafter abbreviated as $AP_4A$), $AP_5A$, diadenosine hexaphosphate (hereinafter abbreviated as $AP_6A$), etc.], and the like.

The source of the HK used in the present invention is not particularly limited and there can be used, for example, HK derived from a microorganism, HK derived from an animal, etc. GK having a higher substrate specificity for glucose than HK can also be used like HK. The source of GK is not particularly limited and there can be used, for example, GK derived from a microorganism of Bacillus genus or the like, GK derived from an animal, etc. Any of these HK's and GK's may be incorporated into the liquid reagent composition for measuring CK activity so that its concentration in a reaction solution for measuring CK activity may be in a concentration range employed in a conventional measuring method. For example, it is incorporated into the liquid reagent composition for measuring CK activity so that its concentration in the reaction solution for measuring CK activity may be usually 0.5 u/ml to 20 u/ml, preferably 0.5 u/ml to 5.0 u/ml. As to the form of the HK or the GK to be incorporated into the liquid reagent composition for measuring CK activity, employment of HK or GK suspended in an ammonium sulfate solution is not very preferable because it is known that ammonium sulfate lowers CK activity by 10 to 15% when its concentration becomes about 50 mM.

Since the presence of a high concentration of CP inhibits CK activity, the CP used in the present invention is incorporated into the liquid reagent composition for measuring CK activity so that its concentration in the reaction solution for measuring CK activity may be usually 5 mM to 70 mM, preferably 30 mM to 50 mM. Since it is well-known in this art that CP is stable in an alkali solution, pH of the reagent containing CP is preferably in the range of 7.5 to 10, more preferably 8 to 9.5.

The source of the G6PDH used in the present invention is not particularly limited and there can be used, for example, G6PDH derived from a microorganism such as Leuconostoc mesenteroides, baker's yeast or the like, G6PDH derived from an animal, etc. The G6PDH is incorporated into the liquid reagent composition for measuring CK activity so that its concentration in the reaction solution for measuring CK activity may be in a concentration range employed in a conventional measuring method. It is incorporated into the liquid reagent composition for measuring CK activity so that its concentration in the reaction solution for measuring CK activity may be usually 0.5 u/ml to 40 u/ml, preferably 1 u/ml to 10 u/ml. As to the form of the G6PDH to be incorporated into the liquid reagent composition for measuring CK activity, employment of G6PDH suspended in an ammonium sulfate solution is not very preferable because it is known that ammonium sulfate lowers CK activity by 10 to 15% when its concentration becomes about 50 mM. When the G6PDH used in the present invention is contaminated with glucose dehydrogenase or NADH (or NADPH) oxidase, the reagent composition tends to be deteriorated or blank values tend to be increased. Therefore, care should be taken.

The NAD (or NADP) and ADP used in the present invention are incorporated into the liquid reagent composition for measuring CK activity so that the concentration of each of them in the reaction solution for measuring CK activity may be in a concentration range employed in a conventional measuring method. The NAD (or NADP) is incorporated into the liquid reagent composition for measuring CK activity so that its concentration in the reaction solution for measuring CK activity may be usually 0.1 mM to 10 mM, preferably 1 mM to 5 mM. The ADP is incorporated into the liquid reagent composition for measuring CK activity so that its concentration in the reaction solution for measuring CK activity may be usually 0.1 mM to 10 mM, preferably 1 mM to 5 mM.

The glucose used as a substrate for HK or GK in the present invention is incorporated into the liquid reagent composition for measuring CK activity so that its concentration in the reaction solution for measuring CK activity may be usually 1 mM to 200 mM, preferably 5 mM to 100 mM.

The magnesium ion used in the present invention is not particularly limited and there can be used all magnesium ions derived from magnesium salts usually used in the art, such as magnesium acetate, magnesium chloride, magnesium sulfate, etc. Since CK activity is known to be non-competitively inhibited by an anion, it is preferable to use, as a magnesium ion source, magnesium acetate or magnesium chloride which, on dissociation, give an anion capable of causing the inhibition only slightly. The concentration of the magnesium salt used cannot be unequivocally determined because it is somewhat varied depending on the kind of the magnesium salt, though usually it is properly chosen in the range of 2 to 30 mM, preferably 5 to 25 mM. Specifically, for example, when magnesium acetate is used, it is incorporated into the liquid reagent composition for measuring CK so that its concentration in the reaction solution for measuring CK activity may be usually 2 mM to 30 mM, preferably 8 mM to 20 mM, when it is considered that the presence of a high concentration of magnesium acetate lowers CK activity and in some cases affects measured values of CK activity in correlation with the concentrations of ADP and a buffer.

Needless to say, the magnesium salts exemplified above as a source of the magnesium ion used in the present invention may be used singly or in proper combination.

The liquid reagent composition for measuring CK of the present invention is used in the form of a two-reagent system composed of a combination of a first reagent comprising ADP, HK (or GK), NAD (or NADP), G6PDH and at least one compound selected from the group consisting of TG, 2ME, and 2MES or its salt, and a second reagent comprising CP and the like with a pH in the range of 7.5 to 10, the glucose and the magnesium ion being separately or in combination incorporated in either one or both of the first reagent and the second reagent.

As to a manner in which the glucose and the magnesium ion are separately or in combination incorporated in either one or both of the first reagent and the second reagent, the combinations described in Table 1 can be exemplified.

TABLE 1

| | First reagent | Second reagent |
|---|---|---|
| 1. | Glucose | Magnesium ion |
| 2. | Magnesium ion | Glucose |
| 3. | Glucose, magnesium ion | Glucose, magnesium ion |
| 4. | Glucose, magnesium ion | — |
| 5. | — | Glucose, magnesium ion |
| 6. | Glucose | Glucose, magnesium ion |
| 7. | Magnesium ion | Glucose, magnesium ion |
| 8. | Glucose, magnesium ion | Glucose |
| 9. | Glucose, magnesium ion | Magnesium ion |

In the measurement of CK activity by use of the two-reagent system, various substances (e.g. bilirubin, hemoglobin, ascorbic acid, chyle, AK, etc.) present in a body fluid used as a sample affect a measuring system in some cases. Therefore, for measuring CK activity with higher precision, the measurement is preferably carried out by a method comprising subtraction of a sample blank value, a so-called double kinetics method. When the measurement is carried out by this method, the glucose and the magnesium ion should be contained in at least the first reagent (as in the combinations 3, 4, 8 and 9 in Table 1).

The liquid reagent composition for measuring CK activity in two-reagent system preferably contains one or more chelating agents for stabilizing the SH compound and preventing the reagent from coloring in an effective concentration. Examples of such chelating agents are EDTA, trans-1,2-diaminocyclohexane-N,N,N',N'-tetraacetic acid monohydrate, 1,3-diamino-2-hydroxypropane-N,N,N',N'-tetracetic acid, ethylenediamine-N,N'-diacetic acid, N-(2-hydroxyethyl)iminodiacetic acid, N-(2-hydroxyethyl) iminodiacetic acid, and salts thereof, e.g. alkali metal salts thereof, ammonium salts thereof.

Since CP is well-known to be stable in an alkali solution, it is preferable that in a reagent composition on the two-reagent system, the pH of the reagent containing CP is made alkaline, for example, in the range of usually 7.5 to 10, preferably 8 to 9.5. However, needless to say, the kind and concentration of a buffer in each of the first reagent and the second reagent should be properly adjusted so that the pH of a mixture of the first reagent and the second reagent, i.e., the pH at the measurement of CK activity may be the optimum pH of CK, for example, a pH in the range of pH 6.0 to 7.2, and it is not desirable to employ a buffer and a buffer concentration which inhibit CK activity in the measurement of CK activity. As a buffer which can be used in the CP-containing reagent for such a purpose, there can be exemplified Bicine, N-[tris(hydroxymethyl)methyl]glycine, etc.

The buffer concentration in the first reagent may be usually 40 mM to 250 mM, preferably 80 mM to 150 mM, and the pH of the first reagent is in the range of usually 6.0 to 7.2, preferably 6.4 to 7.0.

Further, the buffer concentration in the second reagent (that is, CP-containing reagent) may be usually 1 mM to 150 mM, preferably 1 mM to 30 mM, and the pH of the second reagent is in the range of usually 7.5 to 10, preferably 8 to 9.5.

For example, when imidazole is used as a buffer for the first reagent, its concentration in the first reagent is usually 60 mM to 250 mM, preferably 80 mM to 150 mM. When Bicine is used as a buffer for the second reagent, its concentration in the second reagent is usually 1 mM to 100 mM, preferably 1 mM to 30 mM.

To measure CK activity by use of the liquid reagent for measuring CK activity of the present invention, it is sufficient that the measurement is carried out by a conventional procedure.

TG, 2ME, and 2MES or its salt which are used as a CK reactivator in the liquid reagent for measuring CK activity of the present invention have been known as CK reactivators together with other various SH compounds such as NAC, DTT, glutathione, L-cysteine, etc. Of the above various SH compound known as CK reactivators, SH compounds, oxidized products of which do not inhibit CK activity and which can retain a stable CK-reactivating ability for a long period of time in an aqueous solution are unexpectedly only TG, 2ME, and 2MES or its salt which are used in the present invention. On the basis of such information obtained by the present inventors for the first time, the present inventors prepared the present invention's liquid reagent for measuring CK activity which comprises TG, 2ME, and 2MES or its salt, to find that said liquid reagent has long-term stability at liquid state which has been considered difficult to have for conventional reagents for measuring CK activity, namely, said liquid reagent is usable stably for a long period of time e.g. at least 3 months, usually 6 months or more without deterioration in performance characteristics when stored at 10° C. Thus, the present invention has been accomplished.

The liquid reagent kit for measuring CK activity of the present invention is used for measuring CK activity in a body fluid such as serum and can be stored for a long period of time. It comprises a combination of a first reagent container containing
    imidazole-acetate buffer,
    magnesium acetate,
    sodium azide,
    NADP,
    HK,
    G6PDH,
    ADP,
    AMP,
    TG,
    AP$_5$A,
    glucose and
    EDTA, pH 6.0–7.2 a second reagent container containing
    Bicine-sodium hydroxide buffer,
    magnesium acetate,
    sodium azide,
    EDTA,
    glucose and
    CP, pH 7.5–10.0

Preferable properties, specific examples and the like of the individual constituents are as described above. Needless to say, a CK standard material and the like may be combined with said kit if necessary.

The present invention is explained below in further detail with reference to Referential Examples, Examples and Comparative Examples, which are not by way of limitation but by way of illustration.

REFERENCE EXAMPLE 1

Investigation on the inhibitory effect of oxidized products of SH compounds on CK activity

[Oxidized Products]

A 300 mM aqueous solution of each of the following SH compounds was allowed to stand at a high temperature until no SH group was further detected: TG, 2ME, 2MES (sodium salt), NAC, GSH, mercaptosuccinic acid, 1-thio-β-D-glucose disodium salt dihydrate (TDG), 4-amino-6-hydroxy-2-mercaptopyrimidine monohydrate (AHMP), 2-amino-6-mercaptopurine riboside hydrate (AMPR), thiophenol, 2-thiouracil and DTT. Thus, oxidized products of the SH compounds, respectively, were obtained.

[Enzyme Solutions]

NAC (26 mM) as CK reactivator, each 5 mM of SH compound oxidized product obtained above, 2.6 mM of ADP, 3.9 u/ml of HK (available from Oriental Yeast Co., Ltd.), 8.0 u/ml of G6PDH (available from Oriental Yeast Co., Ltd.), 2.6 mM of NADP, 21 mM of glucose, 10 mM of magnesium acetate, 6.5 mM of AMP, 0.013 mM of AP$_5$A, 0.1% (w/v) of sodium azide and 2 mM of EDTA-2Na were dissolved in 128 mM imidazole-acetate buffer (pH 6.7). The thus obtained solutions were adjusted to pH 6.7 with sodium hydroxide to obtain enzyme solutions.

An enzyme solution containing no SH compound oxidized product was prepared as a control standard solution.

[Substrate Solution]

As a substrate solution, there was used a solution prepared by dissolving 155 mM of CP, 21 mM of glucose, 10 mM of magnesium acetate, 0.1% (w/v) of sodium azide and 2 mM of EDTA-2Na in 10 mM Bicine-sodium hydroxide buffer (pH 8.5), and adjusting the resulting solution to pH 9.0 with sodium hydroxide.

[Samples]

Five fresh human serum samples were used.

[Measurement of CK Activity]

To 8 μl of each sample was added 320 μl of each enzyme solution, followed by preincubation for 5 minutes. Then, 80 μl of the substrate solution was added to initiate the reaction and the change of absorbance per minute was measured for 3 minutes from 2 minutes after the addition of the substrate solution. The CK activity value was calculated from the molecular extinction coefficient of the NADPH produced.

As a measuring apparatus, an Autoanalyzer Hitachi Model 7150 was used, and the measurement was carried out at 37° C. by use of dual wavelength ($\lambda_1$=405 nm, $\lambda_2$=340 nm).

Tables 2 and 3 show the CK activity values of the 5 samples in each case and the average thereof.

TABLE 2

| | SH compound oxidized product | | | | | unit (IU/l.) |
|---|---|---|---|---|---|---|
| | No addition of oxidized product | TG oxidized product | 2ME oxidized product | 2MES oxidized product | NAC oxidized product | GSH oxidized product |
| Sample 1 | 156 | 153 | 155 | 155 | 124 | 125 |
| Sample 2 | 428 | 422 | 427 | 418 | 342 | 321 |
| Sample 3 | 112 | 112 | 113 | 114 | 87 | 90 |
| Sample 4 | 332 | 333 | 332 | 335 | 272 | 265 |
| Sample 5 | 100 | 106 | 101 | 98 | 80 | 77 |
| Average | 226 | 226 | 226 | 224 | 181 | 176 |
| % | 100.0 | 100.0 | 100.0 | 99.3 | 80.1 | 77.9 |

TABLE 3

| | SH compound oxidized product | | | | | | unit (IU/l.) |
|---|---|---|---|---|---|---|---|
| | Mercapto-succinic acid | TDG oxidized product | AHMP oxidized product | AMPR oxidized product | Thiophenol oxidized product | 2-Thiouracil oxidized product | DTT oxidized product |
| Sample 1 | 122 | 136 | 161 | 0 | 73 | 143 | 150 |
| Sample 2 | 330 | 388 | 407 | 1 | 180 | 407 | 407 |
| Sample 3 | 98 | 102 | 106 | 0 | 55 | 106 | 108 |
| Sample 4 | 285 | 302 | 322 | 1 | 139 | 314 | 319 |
| Sample 5 | 80 | 90 | 97 | 0 | 50 | 97 | 99 |
| Average | 183 | 204 | 217 | 0 | 99 | 213 | 216 |
| % | 81.0 | 90.2 | 96.0 | 0.2 | 44.1 | 94.6 | 95.9 |

*The values shown as percentages in Tables 2 and 3 are relative values obtained when the average of CK activity values measured by use of the enzyme solution containing no SH compound oxidized product, immediately after the preparation of the solution was taken as 100%.

As is clear from the results shown in Tables 2 and 3, of the various SH compounds, the oxidized products of TG, 2ME and 2MES which are used in the liquid reagent for measuring CK activity of the present invention and the oxidized products of TDG, AHMP, 2-thiouracil and DTT hardly inhibited CK activity.

EXAMPLE 1

[CK Reactivators]

TG, 2ME and 2MES were used as CK reactivators.

[Enzyme Solutions]

One or two SH compounds properly selected from the above-mentioned CK reactivators in predetermined concentrations listed in Table 4, 2.6 mM of ADP, 3.9 u/ml of HK (available from Oriental Yeast Co., Ltd.), 8.0 u/ml of G6PDH (available from Oriental Yeast Co., Ltd.), 2.6 mM of NADP, 21 mM of glucose, 10 mM of magnesium acetate, 6.5 mM of AMP, 0.013 mM of $AP_5A$, 0.1% (w/v) of sodium azide and 2 mM of EDTA-2Na were dissolved in 128 mM imidazole-acetate buffer (pH 6.7). The resulting solution was adjusted to pH 6.7 with sodium hydroxide and stored at a predetermined temperature for a predetermined period. The thus obtained solution were used as enzyme solutions.

[Substrate Solution]

As a substrate solution, there was used a solution prepared by dissolving 155 mM of CP, 21 mM of glucose, 10 mM of magnesium acetate, 0.1% (w/v) of sodium azide and 2 mM of EDTA-2Na in 10 mM Bicine-sodium hydroxide buffer (pH 8.5), and adjusting the resulting solution to pH 9.0 with sodium hydroxide.

[Samples]

Five fresh human serum samples were used.

[Measurement of CK Activity]

To 8 μl of each sample was added 320 μl of each enzyme solution, followed by preincubation for 5 minutes. Then, 80 μl of the substrate solution was added to initiate the reaction and the change of absorbance per minute was measured for 3 minutes from 2 minutes after the addition of the substrate solution. The CK activity value was calculated from the molecular extinction coefficient of the NADPH produced.

As a measuring apparatus, an Autoanalyzer Hitachi Model 7150 was used, and the measurement was carried out at 37° C. by use of dual wavelength ($\lambda_1$=405 nm, $\lambda_2$=340 nm).

Table 4 shows the CK activity values of the 5 samples in each case and the average thereof.

COMPARATIVE EXAMPLE 1

[CK Reactivators]

As CK reactivators, there were used TG, 2ME, TDG, DTT, AHMP and 2-thiouracil, i.e., the SH compounds the oxidized products of which had been found to be not inhibitory to CK activity from the results obtained in Referential Example 1, and NAC, 1-cysteine and GSH which were conventional CK reactivators.

[Enzyme Solutions]

Enzyme solutions were prepared in the same manner as in Example 1 by use of the same reagents as in Example 1 except for using a predetermined concentration(s) of one or two SH compounds properly selected from the above-mentioned CK reactivators, in place of the CK reactivator(s) used in Example 1.

[Substrate Solution]
The same as in Example 1.
[Samples]
The same as in Example 1.
[Measurement of CK Activity]
CK activity was measured in the same manner as in Example 1.

Table 4 shows the CK activity values of the 5 samples in each case and the average thereof.

Table 4 does not show the results obtained by using any of AHMP and 2-thiouracil as a CK reactivator. That is, data were omitted because these compounds had such a low solubility that no accurate measurement could be carried out.

TABLE 4 unit (IU/l)

| | Example 1 | | | | | | | | | | | | Comparative Example 1 NAC (26mM) | | |
|---|---|---|---|---|---|---|---|---|---|---|---|---|---|---|---|
| | TG (100 mM) | | | 2ME (26 mM) | | | 2MES (26 mM) | | | TG (104 mM) 2ME (7 mM) | | | | | |
| CK re-activator Storage conditions | Just after prep-ara-tion | at 10° C. for 1 month | at 20° C. for 1 month | Just after prep-ara-tion | at 10° C. for 1 month | at 20° C. for 1 month | Just after prep-ara-tion | at 10° C. for 1 month | at 20° C. for 1 month | Just after prep-ara-tion | at 10° C. for 1 month | at 20° C. for 1 month | Just after prep-ara-tion | at 10° C. for 1 month | at 20° C. for 1 month |
| Sample 1 | 184 | 183 | 180 | 186 | 186 | 186 | 184 | 184 | 181 | 185 | 183 | 183 | 183 | 184 | 166 |
| Sample 2 | 553 | 556 | 549 | 554 | 559 | 559 | 553 | 548 | 542 | 554 | 556 | 553 | 544 | 550 | 499 |
| Sample 3 | 151 | 154 | 152 | 151 | 155 | 155 | 151 | 147 | 148 | 151 | 154 | 154 | 151 | 152 | 136 |
| Sample 4 | 58 | 57 | 57 | 58 | 59 | 58 | 58 | 55 | 55 | 58 | 57 | 57 | 56 | 55 | 50 |
| Sample 5 | 88 | 88 | 88 | 89 | 89 | 89 | 88 | 85 | 87 | 90 | 88 | 87 | 87 | 88 | 78 |
| Average | 207 | 208 | 206 | 208 | 210 | 209 | 207 | 204 | 203 | 208 | 208 | 207 | 204 | 206 | 186 |
| % | 101.4 | 101.9 | 100.9 | 101.9 | 102.8 | 102.4 | 101.4 | 99.9 | 96.3 | 101.9 | 101.9 | 101.4 | 100.0 | 101.0 | 91.2 |

| | Comparative Example 1 | | | | | | | | | | | | | |
|---|---|---|---|---|---|---|---|---|---|---|---|---|---|---|
| | L-cysteine (6.5 mM) | | GSH (12 mM) | | TDG (5 mM) | | DTT (6.5 mM) | | NAC (26 mM) GSH (5 mM) | | NAC (26 mM) TG (5 mM) | | NAC (26 mM) 2ME (5 mM) | |
| CK re-activator Storage conditions | at 10° C. for 1 month | at 20° C. for 1 month | at 10° C. for 1 month | at 20° C. for 1 month | at 10° C. for 1 month | at 20° C. for 1 month | at 10° C. for 1 month | at 20° C. for 1 month | at 10° C. for 1 month | at 20° C. for 1 month | at 10° C. for 1 month | at 20° C. for 1 month | at 10° C. for 1 month | at 20° C. for 1 month |
| Sample 1 | 140 | 52 | 169 | 146 | 0 | 0 | 183 | 77 | 177 | 149 | 162 | 142 | 185 | 171 |
| Sample 2 | 437 | 175 | 518 | 465 | 3 | 4 | 549 | 330 | 534 | 455 | 502 | 433 | 549 | 509 |
| Sample 3 | 110 | 33 | 142 | 116 | 1 | 2 | 153 | 19 | 145 | 120 | 130 | 113 | 153 | 139 |
| Sample 4 | 42 | 12 | 48 | 42 | 0 | 0 | 56 | 5 | 52 | 44 | 42 | 41 | 55 | 51 |
| Sample 5 | 63 | 19 | 81 | 68 | 0 | 0 | 89 | 12 | 82 | 68 | 71 | 65 | 88 | 81 |
| Average | 158 | 58 | 192 | 167 | 1 | 1 | 206 | 89 | 198 | 167 | 181 | 159 | 206 | 190 |
| % | 77.5 | 28.4 | 94.1 | 81.9 | 0.4 | 0.6 | 101.0 | 43.6 | 97.1 | 81.9 | 88.7 | 77.9 | 101.0 | 93.1 |

*The values shown as percentages in Table 4 are relative values obtained when the average of CK activity values measured by use of the enzyme solution containing NAC as a CK reactivator, immediately after the preparation of the solution in Comparative Example 1 was taken as 100%.

As is clear from the results shown in Table 4, the CK reactivators used in the liquid reagent for measuring CK activity of the present invention are equal in CK-reactivating ability to NAC, a conventional CK reactivator. It can also be seen that of the various SH compounds including NAC, compounds capable of retaining CK-reactivating ability for a long period of time when added to an aqueous solution are only TG, 2ME and 2MES, i.e., the CK reactivators according to the present invention.

In addition, the results shown in Table 4 indicate the following: when a combination of NAC and TG was used as a CK reactivator, the CK-reactivating ability after 1 month of storage was deteriorated at both 10° C. and 20° C.; on the other hand, when a combination of NAC and 2ME was used, the CK-reactivating ability was stable even after 1 month of storage at 10° C. but the CK-reactivating ability after 1 month of storage was clearly deteriorated at 20° C.

From these facts, it can be seen that in the conventional way of thinking on condition that NAC is used as the main component of a CK reactivator, a liquid reagent for measuring CK activity which is stable for a long period of time is difficult to prepare.

When the results obtained in Referential Example 1 are taken into consideration, it can be seen that among SH compounds, oxidized products of which do not inhibit CK activity, there are compounds unsuitable as a CK reactivator for a liquid reagent for measuring CK activity, i.e., compounds incapable of retaining CK-reactivating ability in a solution for a long period of time, such as TDG and DTT, and compounds incapable of exhibiting a sufficient CK-reactivating ability because of their low solubility and the like, such as AHMP and 2-thiouracil.

From the above facts, it is considered that a CK reactivator for a liquid reagent required to have long-term storage stability should have, for example, the following properties: it has at least a sufficient CK-reactivating ability, it can retain a stable CK-reactivating ability in an aqueous solution for a long period of time, and its oxidized product does not inhibit CK activity. It can be seen that TG, 2ME and 2MES or its salt, i.e., the CK reactivators according to the present invention satisfy all of these conditions.

EXAMPLE 2

[Enzyme Solution]

An enzyme solution was prepared in the same manner as in Example 1 by use of the same reagents as in Example 1 except for using 100 mM of TG in place of the CK reactivator(s) used in Example 1.

[Substrate Solution]

The same as in Example 1.

[Samples]

Different 10 fresh human serum samples were used for different measuring operations.

[Measurement of CK Activity]

CK activity was measured by the same procedure as described in Example 1 except for using the above-mentioned enzyme solution and substrate solution, both solutions stored at 10° C. for a predetermined time, and each of the above-mentioned samples.

Table 5 shows the average of the CK activity values of the 10 samples in each case.

COMPARATIVE EXAMPLE 2

[Enzyme Solution]

An enzyme solution was prepared in the same manner as in Example 1 by use of the same reagents as in Example 1 except for using 26 mM of NAC in place of the CK reactivator(s) used in Example 1.

[Substrate Solution]

The same as in Example 1.

[Samples]

The same as in Example 2.

[Measurement of CK Activity]

CK activity was measured by the same procedure as described in Example 1 except for using the above-mentioned enzyme solution and substrate solution, both solutions stored at 10° C. for a predetermined period, and each of the above-mentioned samples.

Table 5 shows the average of the CK activity values of the 10 samples in each case.

As a result of investigation of the calibration range, it was confirmed that the liquid reagent for measuring CK of the present invention has the same calibration range as immediately after its preparation, even after 7 months of storage at 10° C., namely, it retains the same performance characteristics as immediately after its preparation.

EXAMPLE 3

A typical example of liquid-reagent kit which is used for measuring CK activity in a body fluid such as serum and can be stored for a long period of time is as follows:

(1) First reagent:
   imidazole-acetate buffer,
   magnesium acetate,
   sodium azide,
   NADP,
   HK,
   G6PDH,
   ADP,
   AMP,
   TG,
   $AP_5A$,
   glucose,
   EDTA.
   pH 6.0–7.2

(2) Second reagent:
   Bicine-sodium hydroxide buffer,
   magnesium acetate,
   sodium azide,
   EDTA,
   glucose,
   CP.
   pH 7.5–10.0

The present invention provides a liquid reagent for measuring CK activity in a body fluid such as serum, and the liquid reagent for measuring CK activity of the present invention is markedly effective in that it can be stored for such a long period of time that when stored at a low temperature, for example, 10° C., it can be used for at least 3 months, usually 6 months or more, without deterioration in performance characteristics.

TABLE 5

|  | Just after preparation | After 1 month of storage | | After 3 month of storage | | After 6 month of storage | | unit (IU/l.) After 7 month of storage | |
| --- | --- | --- | --- | --- | --- | --- | --- | --- | --- |
|  |  | At the time of use | at 10° C. for 1 month | At the time of use | at 10° C. for 3 month | At the time of use | at 10° C. for 6 month | At the time of use | at 10° C. for 7 month |
| Example 2 TG | 240 | 204 | 202 (99.0%) | 200 | 198 (99.0%) | 168 | 168 (100.0%) | 192 | 190 (99.0%) |
| Comparative Example 2 NAC | 234 | 196 | 190 (96.9%) | 192 | 146 (76.0%) | 162 | 64 (39.5%) | 192 | 62 (32.3%) |

*The values in the parentheses are relative values obtained when the average of CK activity values measured by using the enzyme solution prepared at the time of use was taken as 100%.

As is clear from the results shown in Table 5, the conventional reagent for measuring CK activity obtained by using NAC as a CK reactivator gave a markedly lowered measured value of CK activity after 3 months of storage at 10° C. and hence was difficult to use. By contrast, the liquid reagent for measuring CK of the present invention gave an uninfluenced measured value of CK activity even after 7 months of storage at 10° C., indicating that it retained the same performance characteristics as immediately after its preparation.

In the present specification, abbreviations not specified before mean as follows:

| | |
| --- | --- |
| CP | creatine phosphate |
| ADP | adenosine 5'-diphosphate |
| HK | hexokinase |
| GK | glucokinase |
| NAD | nicotinamide adenine dinucleotide |

| | |
|---|---|
| NADP | nicotinamide adenine dinucleotide phosphate |
| G6PDH | glucose-6-phosphate dehydrogenase |

What is claimed is:

1. A liquid reagent composition for measuring creatine kinase activity, which comprises a first liquid reagent comprising adenosine 5'-diphosphate, hexokinase or glucokinase, nicotinamide adenine dinucleotide or nicotinamide adenine dinucleotide phosphate, glucose-6-phosphate dehydrogenase, and at least one compound selected from the group consisting of thioglycerol, 2-mercaptoethanol, and 2-mercaptoethanesulfonic acid or its salt;

a second liquid reagent comprising creatine phosphate and having a pH of 7.5 to 10.0; and glucose and magnesium ion being separately, or in combination, incorporated in either one or both of the first liquid reagent and the second liquid reagent:

wherein the concentration of thioglycerol is 10 mM or more, the concentration of 2-mercaptoethanol is 5 mM or more and the concentration of 2-mercaptoethanesulfonic acid or a salt thereof is 5 mM or more in a reaction solution for measuring creatine kinase activity.

2. A liquid reagent composition for measuring creatine kinase activity according to claim 1, wherein the glucose and the magnesium ion are incorporated in the first reagent.

3. A liquid reagent composition for measuring creatine kinase activity according to claim 2, wherein the magnesium ion is derived from at least one member selected from the group consisting of magnesium acetate and magnesium chloride.

4. A liquid reagent composition for measuring creative kinase activity according to claim 1, wherein the magnesium ion is derived from at least one member selected from the group consisting of magnesium acetate and magnesium chloride.

5. A liquid reagent composition for measuring creatine kinase activity, which comprises a first liquid reagent comprising adenosine 5'-diphosphate, hexokinase or glucokinase, nicotinamide adenine dinucleotide or nicotinamide adenine dinucleotide phosphate, glucose-6-phosphate dehydrogenase, and at least one compound selected from the group consisting of thioglycerol, 2-mercaptoethanol, and 2-mercaptoethanesulfonic acid or a salt thereof;

a second liquid reagent comprising creatine phosphate and having a pH of 7.5 to 10.0; and glucose and magnesium ion being separately or in combination incorporated in either one or both of the first liquid reagent and the second liquid reagent;

wherein the concentration of thioglycerol is 10 mM or more, the concentration of 2-mercaptoethanol is 5 mM or more, and that concentration of 2-mercaptoethanesulfonic acid or a salt thereof is 5 mM or more in a reaction solution for measuring creatine kinase activity;

wherein the first liquid reagent and the second liquid reagent are capable of being stored for at least 3 months at 10° C. without decreasing their ability to measure creatine kinase activity.

6. A liquid reagent composition for measuring creatine kinase activity, which comprises a first liquid reagent comprising adenosine 5'-diphosphate, hexokinase, nicotinamide adenine dinucleotide or nicotinamide adenine dinucleotide phosphate, glucose-6-phosphate dehydrogenase, and at least one compound selected from the group consisting of thioglycerol, 2-mercaptoethanol, and 2-mercaptoethanesulfonic acid or a salt thereof;

a second liquid reagent comprising creatine phosphate and having a pH of 7.5 to 10.0; and glucose and magnesium ion being separately, or in combination, incorporated in either one or both of the first liquid reagent and the second liquid reagent;

wherein concentration of thioglycerol is 10 mM or more, the concentration of 2-mercaptoethanol is 5 mM or more, and the concentration of said 2-mercaptoethanesulfonic acid or a salt thereof is 5 mM or more in a reaction solution for measuring creatine kinase activity;

wherein the first liquid reagent and the second liquid reagent are capable of being stored for at least 3 months at 10° C. without decreasing their ability to measure creatine kinase activity.

7. A liquid reagent composition for measuring creatine kinase activity, which comprises a first liquid reagent comprising adenosine 5'-diphosphate, glucokinase, nicotinamide adenine dinucleotide phosphate, glucose-6-phosphate dehydrogenase, and at least one compound selected from the group consisting of thioglycerol, 2-mercaptoethanol, and 2-mercaptoethanesulfonic acid or a salt thereof;

a second liquid reagent comprising creatine phosphate and as a buffer N,N-bis(2-hydroxyethyl)glycine or N-[tris(hydroxymethyl)methyl]glycine, and having a pH of 7.5 to 10.0; and glucose and magnesium ion being separately or in combination incorporated in either one or both of the first liquid reagent and the second liquid reagent;

wherein the concentration of thioglycerol is 10 mM or more, the concentration of 2-mercaptoethanol is 5 mM or more, and the concentration of 2-mercaptoethanesulfonic acid or a salt thereof is 5 mM or more in a reaction solution for measuring creatine kinase activity, wherein the first liquid reagent and the second liquid reagent are capable of being stored for at least 3 months at 10° C. without decreasing their ability to measure kinase activity.

* * * * *